US009010339B2

(12) United States Patent
Dube et al.

(10) Patent No.: US 9,010,339 B2
(45) Date of Patent: Apr. 21, 2015

(54) METHOD FOR PRODUCING TRIACETIN FROM TOBACCO

(75) Inventors: Michael Francis Dube, Winston-Salem, NC (US); William Coleman, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 979 days.

(21) Appl. No.: 13/117,655

(22) Filed: May 27, 2011

(65) Prior Publication Data

US 2012/0298125 A1 Nov. 29, 2012

(51) Int. Cl.
| | |
|---|---|
| C07C 67/08 | (2006.01) |
| C07C 69/34 | (2006.01) |
| A24B 15/18 | (2006.01) |
| A24B 15/20 | (2006.01) |
| A24B 15/24 | (2006.01) |
| A24B 15/28 | (2006.01) |
| C07C 29/09 | (2006.01) |
| A24B 15/30 | (2006.01) |
| C07C 51/09 | (2006.01) |

(52) U.S. Cl.
CPC .............. *C07C 29/095* (2013.01); *C07C 67/08* (2013.01); *A24B 15/24* (2013.01); *A24B 15/30* (2013.01); *A24B 15/302* (2013.01); *C07C 51/09* (2013.01)

(58) Field of Classification Search
USPC ............. 435/18, 19, 132, 135, 136, 155, 158, 435/159, 195–198; 131/290, 297, 347, 352, 131/356; 560/190, 202, 204; 426/417, 419, 426/506, 507
See application file for complete search history.

(56) References Cited

U.S. PATENT DOCUMENTS

| 1,463,209 | A | * | 7/1923 | Haggenmacher | 562/607 |
|---|---|---|---|---|---|
| 2,173,124 | A | * | 9/1939 | Conklin et al. | 560/254 |
| 2,331,965 | A | * | 10/1943 | Dreyfus | 423/283 |
| 2,822,306 | A | * | 2/1958 | Thienemann et al. | 131/352 |
| 3,166,078 | A | | 1/1965 | Parmele et al. | |
| 4,056,442 | A | * | 11/1977 | Huang et al. | 435/15 |
| 4,715,390 | A | | 12/1987 | Nichols et al. | |
| 4,783,418 | A | * | 11/1988 | Long et al. | 436/96 |
| 4,986,286 | A | | 1/1991 | Roberts et al. | |
| 5,038,802 | A | | 8/1991 | White et al. | |
| 5,074,319 | A | | 12/1991 | White et al. | |
| 5,251,649 | A | * | 10/1993 | Cho et al. | 131/296 |
| 7,237,558 | B2 | | 7/2007 | Clark et al. | |
| 7,579,493 | B2 | * | 8/2009 | Gutsche et al. | 554/174 |
| 7,793,665 | B2 | | 9/2010 | Dube et al. | |

FOREIGN PATENT DOCUMENTS

| CN | 102020558 A | * | 4/2011 |
|---|---|---|---|
| EP | 0244208 A2 | | 11/1987 |
| JP | 11308987 A | | 11/1999 |

OTHER PUBLICATIONS

Derwent Abstract of CN 102020558 A, 2014.*
Moldoveanu, "5. Profiling of lipids from fruit and seed extracts", Lipidomics: Sea Food, Marine Based Dietary Supplement, Fruit and Seed, 2012: pp. 73-123, Ed. Su Chen [online], Retrieved from the Internet, [retrieved Oct. 21, 2014], <URL: http://www.trnres.com/ebook/uploads/suchencontent/T_13743193085%20Su%20Chen.pdf>.*
Korean Intellectual Property Office; The International Search Report and the Written Opinion of the International Searching Authority, or the Declaration; International Search Report and Written Opinion; Oct. 12, 2012; pp. 1-9; Korean Intellectual Property Office; Korea.

* cited by examiner

*Primary Examiner* — Dennis Cordray
(74) *Attorney, Agent, or Firm* — Middleton Reutlinger; George D. McClure; John F Salazar

(57) ABSTRACT

A method for producing triacetin from one or more plants of genus *Nicotiana* is provided. The triacetin can be derived inter alia from *Nicotiana* species biomass or from seed. In certain embodiments, the triacetin is produced by condensation of glycerin, generated by hydrolysis of acylglycerol-containing starting material derived from tobacco biomass or seed, and acetic acid, also derived from tobacco biomass or seed. The invention also provides articles and compositions including tobacco articles and tobacco compositions that include triacetin produced from one or more plants of genus *Nicotiana*.

20 Claims, No Drawings

METHOD FOR PRODUCING TRIACETIN FROM TOBACCO

FIELD OF THE INVENTION

The present invention relates to products made or derived from tobacco or, more generally, made or derived from any biomass derived from any one or more species of genus *Nicotiana*, or that otherwise incorporate tobacco, and are intended for human consumption. Of particular interest are ingredients or components obtained or derived from plants or portions of plants from the *Nicotiana* species.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco, and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. See also, Leffingwell et al., *Tobacco Flavoring for Smoking Products*, R. J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Publication No. 2004/0173228 to Coleman, III; and U.S. application Ser. No. 12/191,751 to Coleman, III et al., filed Aug. 14, 2008, each of which is incorporated herein by reference. Additionally, examples of representative components that can be employed as so-called natural tar diluents in tobacco products are set in PCT WO 2007/012980 to Lipowicz, which is incorporated herein by reference.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. Appl. Pub. Nos. 2005/0244521 to Strickland et al.; 2008/0196730 to Engstrom et al.; and 2009/0293889 to Kumar et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

Found as an ingredient in any of a number of tobacco product formulations is triacetin (CAS 102-76-1). Triacetin is also known, for example, as 1,2,3-propanetriol triacetate; glyceryl triacetate; triacetyl glycerine; or glycerolum triacetas. While it may serve any of a number of functions in tobacco product formulations, triacetin is known in the art to serve as a humectant, a plasticizer, or a solvent. In addition, triacetin may function as a fixative or an antifungal. A liquid at typical room temperature, triacetin is colorless and viscous.

Triacetin is useful as a component of a variety of tobacco products or as an ingredient in the processing of tobacco. See, for example, U.S. Pat. No. 3,166,078 to Parmele et al.; U.S. Pat. No. 4,715,390 to Nichols et al.; U.S. Pat. No. 5,038,802 to White et al.; U.S. Pat. No. 7,237,558 to Clark et al.; and U.S. Pat. No. 7,793,665 to Dube et al., each of which is incorporated herein by reference.

As it should be clear from the foregoing that triacetin is useful in the formulation of various tobacco products, it can also be seen that it would accordingly be desirable to provide a method for producing triacetin from tobacco, that is, in particular, from *Nicotiana* species, for use, inter alia, in tobacco compositions utilized in a variety of tobacco products or in the processing of tobacco.

SUMMARY OF THE INVENTION

The present invention provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products. The invention also provides methods for isolating components from *Nicotiana* species (e.g., tobacco materials), and methods for processing those components and tobacco materials incorporating those components. For example, tobacco-derived materials can be prepared by subjecting at least a portion of a tobacco plant (e.g., leaves, stalks, roots, or stems) to a separation process, which typically can include multiple sequential extraction steps, in order to isolate desired components of the tobacco material.

When used in connection with the invention, the term "acylglycerol" denotes any one or more of the following: monoacylglycerol; diacylglycerol; triacylglycerol.

When used in connection with the invention, the term "biomass" denotes one or more portions of a plant, and in particular denotes substantially the entirety of the superterranean portion of a plant, optionally including some or all of the subterranean portion of a plant. Accordingly, the term "biomass" may refer to leaf or to seed or to any other superterranean portion of a plant, or to any combination thereof, optionally including some or all of the subterranean portion of a plant.

When used in connection with the invention, the term "one or more plants of genus *Nicotiana*" denotes any one or more plants of the genus *Nicotiana* of family Solanaceae, including, for example, any one or more of the following: *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, and N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina,* and *N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. Solanifolia, N. spegazzinii.*

When used in connection with the invention, "alkali metal hydroxide" denotes any one or more of the compounds having formula MOH where M is Li, Na, K, Rb, Cs, or Fr.

When used in connection with the invention, "alkaline earth oxide or hydroxide" denotes any one or more of the compounds having formula MO or $M(OH)_2$ where M is Be, Mg, Ca, Sr, Ba, or Ra. Accordingly, for example, when used in connection with the invention, "contacting an acylglycerol-containing first starting material derived from one or more plants of genus *Nicotiana* and/or from tobacco biomass with a composition comprising an alkaline earth oxide or hydroxide" denotes contacting an acylglycerol-containing first starting material derived from one or more plants of genus *Nicotiana* and/or from tobacco biomass with any one or more of the compounds having formula MO or $M(OH)_2$ where M is Be, Mg, Ca, Sr, Ba, or Ra.

When used in connection with the invention, "mineral acid" denotes an inorganic acid and accordingly can refer, for example, to any one or more of the following: sulfuric acid; phosphoric acid; nitric acid; chloric acid; hydrofluoric acid; hydrochloric acid; hydrobromic acid; hydroiodic acid; chromic acid; sulfurous acid; phosphorous acid; nitrous acid; a halogensulfonic acid $HSO_3X$ wherein X is halogen; perchloric acid; perbromic acid; periodic acid; hydrogen sulfide; hypophosphorous acid; tetrafluoroboric acid; hexafluorophosphoric acid. Accordingly, for example, when used in connection with the invention, "acidic conditions" denotes, inter alia, conditions obtained by contacting a composition, such as a reactant, with a mineral acid, such as concentrated sulfuric acid, and denotes more generally conditions understood by a person skilled in the art to be acidic conditions: conditions in which pH is acidic, that is, less than 7, rather than alkaline, that is, greater than 7. When used in connection with the invention, "transition metal oxide" denotes, inter alia, $ZrO_2$, $WO_3$, $TiO_2$, or $MoO_3$, and denotes more generally a composition understood by a person skilled in the art to be a transition metal oxide.

When used in connection with the invention, "esterase" denotes any one or more enzymes catalyzing hydrolysis of an ester linkage. For example, "esterase" can refer to any one or more enzymes belonging to EC 3.1 (enzymes acting on ester bonds), including, in particular, any one or more enzymes belonging to EC 3.1.1 (carboxylic ester hydrolases). "Esterase" can accordingly refer, for example, to any one or more enzymes belonging to any of the following: EC 3.1.1.1 (carboxylesterases); EC 3.1.1.3 (triacylglycerol lipases); EC 3.1.1.6 (acetylesterases); EC 3.1.1.23 (acylglycerol lipases).

The use of *Nicotiana*-derived (e.g., tobacco-derived) materials of the present invention enables the preparation of tobacco compositions for smoking articles or smokeless tobacco compositions that are derived substantially or even entirely from *Nicotiana* materials. For example, a tobacco composition can incorporate tobacco or tobacco-derived material of some form, including isolated components from *Nicotiana* species, such that at least about 80 weight percent, more typically at least about 90 weight percent, or even at least about 95 weight percent (on a dry weight basis), of that tobacco composition consists of tobacco-derived material.

It has been recognized that there is a need to make fuller use of material or substance from tobacco, and in particular from plants or portions of plants from the *Nicotiana* species. Readily available starting materials or inputs from plants or portions of plants from the *Nicotiana* species, such starting materials or inputs being useful in particular for inclusion as starting materials or inputs in a process whereby material or substance from tobacco can be more fully utilized, include inter alia tobacco biomass and tobacco seed. Tobacco biomass can include for example the entirety of the substance of a tobacco plant that has been harvested whole. Tobacco biomass can include for example essentially all of the superterranean parts of a tobacco plant and optionally can include some or all of the subterranean parts of a tobacco plant. Tobacco biomass can include for example the solid portion of a tobacco plant that has been harvested whole, or the solid portion of essentially all of superterranean parts of a tobacco plant, and from which so-called "green juice" has been expelled for example through the action of a screw press. Tobacco biomass can include for example such a solid portion from which at least a portion of the water has been removed by drying. A tobacco seed may occupy only a very small volume, such as a fraction of a cubic millimeter. For this reason, it is typically practical to collect a plurality of tobacco seeds when it is chosen to harvest tobacco seed.

Among ways in which fuller use can be made of material or substance from tobacco, and in particular from plants or portions of plants from the *Nicotiana* species, are various chemical transformations to which plants or portions of plants from the *Nicotiana* species can be subjected. Such chemical transformations may result in outputs or products having one or more desired or favorable properties. Such outputs or products may themselves be useful as starting material or inputs for further useful processes. Among chemical transformations to which plants or portions of plants from the *Nicotiana* species can be subjected are hydrolyses, including, for example, acid-catalyzed hydrolyses and base-catalyzed hydrolyses. Acid-catalyzed hydrolyses of esters and base-catalyzed hydrolyses of esters are known in the art. An ester which may be subject to hydrolysis includes an ester found at the sn-1, sn-2 or sn-3 position of a triacylglycerol, of a diacylglycerol, or of a monoacylglycerol, such as, in particular, a triacylglycerol, diacylglycerol or monoacylglycerol present in or derived from a tobacco plant or any portion thereof, including, for example, tobacco biomass or a tobacco seed.

Various embodiments of hydrolyses of esters, including acid-catalyzed hydrolyses of esters and base-catalyzed hydrolyses of esters, are known in the art. An acid suitable for an acid-catalyzed hydrolysis of an ester, such as an ester in a triacylglycerol, a diacylglycerol, or a monoacylclycerol, may be a mineral acid. A base suitable for a base-catalyzed hydrolysis of an ester, such as an ester in a triacylglycerol, a diacylglycerol, or a monoacylclycerol, may be a hydroxide of a Group 1 alkali metal monovalent cation, such as lithium hydroxide, sodium hydroxide, or potassium hydroxide.

It is known in the art that the intermediary metabolism of plants, including, inter alia, plants of genus *Nicotiana*, produces acetate. See, for example, Hoskin et al. (1953), American Journal of Botany, Vol. 40, No. 7, pp. 502 ff. The acetyl moiety is present within the ubiquitous intermediate acetyl coenzyme A, which participates in a variety of metabolic reactions. Accordingly, acetate may readily be prepared from a plant source, such as from a plant source from any of the *Nicotiana* species.

Conditions for condensation reactions of polyhydroxy alcohols such as glycerin with acids such as acetic acid are known in the art. See, for example, Gelosa et al. (2003), Industrial and Engineering Chemical Research, Vol. 42, No. 25, pp. 6536 ff.; Ferreira et al. (2009), Catalysis Communications, Vol. 10, No. 5, pp. 481 ff.; Liu et al. (2011), Green Chemistry, Vol. 13, No. 3, pp. 697 ff.

In an aspect, the invention provides a tobacco composition for use in a smoking article or a smokeless tobacco composition comprising a tobacco material and a triacetin-containing component derived from biomass or a seed of the *Nicotiana* species, wherein the triacetin-containing component comprises triacetin.

In certain embodiments, a glycerin-containing component according to the invention is formed using techniques adapted for expressing lipids from biomass or seed, such as high pressure squeezing or cold pressing. Alternatively, a glycerin-containing component according to the invention is formed by extracting components from biomass or seed using appropriate extraction techniques and solvents. Exemplary solvents include hydrocarbons such as heptane and hexane. Other separation processes can be used, such as chromatography, distillation, filtration, recrystallization, solvent-solvent partitioning, and combinations thereof. A glycerin-containing component formed using an extraction process can be either the solvent-soluble portion or the insoluble residue of biomass or seed material remaining after solvent extraction. A glycerin-containing component formed using a pressing process may be inter alia a lipid-containing portion of biomass or seed expressed from pressed biomass or seed material.

In certain embodiments, an acetate-containing component according to the invention is formed using distillation techniques adapted for obtaining acetic acid from biomass or one or more anatomical parts of a plant. Alternatively, an acetate-containing component according to the invention is formed by extracting components from biomass or one or more anatomical parts of a plant using appropriate extraction techniques and solvents. Other separation processes can be used, such as chromatography, filtration, recrystallization, solvent-solvent partitioning, and combinations thereof. An acetate-containing component formed using an extraction process can be either the solvent-soluble portion or the insoluble residue of biomass or other plant material remaining after solvent extraction.

A glycerin-containing component according to the invention comprises glycerin, useful for the production of triacetin. Likewise, an acetate-containing component according to the invention comprises acetate, also useful for the production of triacetin. It will accordingly be seen that, when used in connection with the invention, an "acetate-containing component" may comprise acetic acid or a salt of acetic acid.

A triacetin-containing component according to the invention can be used as such, or in the form of a chemically transformed triacetin-containing component. For example, a chemical transformation of a triacetin-containing component may include acid/base reaction, hydrolysis, thermal treatment, enzymatic treatment, and combinations of such steps.

In a preferred embodiment, a triacetin-containing component according to the invention is made from a glycerin-containing component derived from biomass or one or more anatomical parts of tobacco and an acetate-containing component derived from biomass or one or more anatomical parts of tobacco.

The invention also provides smoking articles and smokeless tobacco compositions that include a triacetin-containing component as described herein. For example, a tobacco composition can incorporate a triacetin-containing component within a casing formulation or a top dressing formulation applied to tobacco strip or as a component of a reconstituted tobacco material.

The invention, in an aspect, relates to a method for preparing a triacetin-containing component from biomass or one or more anatomical parts of the *Nicotiana* species. In a particular preferred embodiment, a method for preparing a triacetin-containing component according to the invention comprises (1) isolating an acylglycerol-containing fraction from harvested biomass or seed of the *Nicotiana* species by subjecting the harvested biomass or seed or a portion thereof to cold pressing, solvent extraction, chromatography, distillation, filtration, recrystallization, solvent-solvent partitioning, or a combination thereof to form an isolated acylglycerol-containing fraction; (2) chemically transforming the acylglycerol-containing fraction by subjecting the acylglycerol-containing fraction to hydrolysis, thereby forming a glycerin-containing component; (3) isolating an acetate-containing component from harvested biomass or one or more anatomical parts of the *Nicotiana* species by subjecting the harvested biomass or one or more anatomical parts or a portion thereof to cold pressing, solvent extraction, chromatography, distillation, filtration, recrystallization, solvent-solvent partitioning, or a combination thereof to form an isolated acetate-containing component; (4) reacting the glycerin-containing component with the acetate-containing component under conditions favoring esterification, thereby forming a triacetin-containing component. The method can further include the step of adding a triacetin-containing component according to the invention to a tobacco composition adapted for use in a smoking article or a smokeless tobacco composition.

In connection with the invention it is accordingly found that a chemical transformation including an ester-hydrolysis treatment of plants or portions of plants from the *Nicotiana* species results in formation of a composition comprising glycerin and from which glycerin can be isolated; that a chemical transformation including a distillation of plants or portions of plants from the *Nicotiana* species results in formation of a composition comprising acetate and from which acetate can be isolated; and that an esterification reaction of glycerin so isolated and acetate so isolated results in formation of triacetin.

Accordingly, in one aspect, the invention provides a method of producing triacetin from tobacco. Such triacetin is suitable for use in, on, or around a smoking article or a smokeless tobacco composition comprising a tobacco material and a component derived from the *Nicotiana* species, wherein the component is derived from the *Nicotiana* species.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Of particular interest are *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, and N. x sanderae*. Also of interest are *N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina, and N. wigandioides*. Other plants from the *Nicotiana* species include *N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia* and *N. spegazzinii*.

*Nicotiana* species can be derived using genetic-modification or crossbreeding techniques (e.g., tobacco plants can be genetically engineered or crossbred to increase or decrease production of certain components or to otherwise change certain characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al.; and U.S. Pat. No. 7,230,160 to Benning et al.; US Patent Appl. Pub. No. 2006/0236434 to Conkling et al.; and PCT WO 2008/103935 to Nielsen et al.

For the preparation of smokeless and smokable tobacco products, it is typical for harvested plants of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. See, also, for example, U.S. Pat. No. 7,650,892 to Groves et al., which is incorporated herein by reference. Representative techniques and conditions for air curing tobacco are set forth in Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Preferably, harvested tobaccos that are cured are then aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing seeding, is commencing flowering, or the like.

At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position. After harvest, the plant of the *Nicotiana* species, or portion thereof, can be used in a green form (e.g., tobacco can be used without being subjected to any curing process). For example, tobacco in green form can be frozen, freeze-dried, subjected to irradiation, yellowed, dried, cooked (e.g., roasted, fried or boiled), or otherwise subjected to storage or treatment for later use. Such tobacco also can be subjected to aging conditions.

In accordance with the present invention, a tobacco product incorporates tobacco that is combined with some form of biomass or one or more anatomical parts obtained from, or derived from, a plant of at least one *Nicotiana* species. That is, a portion of a tobacco product according to the invention can be composed of some form of biomass or one or more anatomical parts of a *Nicotiana* species, such as parts or pieces of biomass or one or more anatomical parts, or processed materials incorporating processed biomass or one or more anatomical parts or components thereof. At least a portion of the tobacco product can be composed of components of biomass or one or more anatomical parts, such as ingredients removed from biomass or one or more anatomical parts (e.g., by extraction, distillation, or other types of processing techniques). At least a portion of the tobacco product can be composed of components derived from biomass or one or more anatomical parts, such as components collected after subjecting biomass or one or more anatomical parts to chemical reaction or after subjecting components collected from biomass or one or more anatomical parts to chemical reaction (e.g., acid/base reaction conditions or enzymatic treatment).

The *Nicotiana* species can be selected for the type of biomass or anatomical part that it produces. For example, plants can be selected on the basis that those plants produce relatively abundant biomass or seed, produce biomass or seed that incorporate relatively high levels of specific desired components, and the like.

The *Nicotiana* species of plant can be grown under agronomic conditions so as to promote development of biomass or one or more anatomical parts. Tobacco plants can be grown in greenhouses, growth chambers, or outdoors in fields, or grown hydroponically.

According to the invention biomass or one or more anatomical parts are harvested from the *Nicotiana* species of plant. The manner by which biomass or one or more anatomical parts are harvested can vary. Typically, essentially all the biomass or anatomical parts can be harvested, and employed as such.

The time of harvest during the life cycle of the plant can vary. For example, biomass or one or more anatomical parts can be harvested when immature. Alternatively, biomass or one or more anatomical parts can be harvested after the point that the plant has reached maturity.

The post-harvest processing of biomass or one or more anatomical parts can vary. After harvest, the biomass or one or more anatomical parts, or portion thereof, can be used in the harvested form (e.g., the biomass can be used without being subjected to any curing and/or aging process steps). For example, biomass or one or more anatomical parts can be used without being subjected to significant storage, handling or processing conditions. In certain situations, it is preferable that the fresh biomass or one or more anatomical parts be used virtually immediately after harvest. Alternatively, for example, biomass or one or more anatomical parts can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

Harvested biomass or seed can be physically processed. Biomass or one or more anatomical parts, or one or more parts thereof, can be further subdivided into parts or pieces (e.g., biomass or seed can be comminuted, pulverized, milled or ground into pieces or parts that can be characterized as granules, particulates or fine powders). Biomass or one or more anatomical parts, or one or more parts thereof, can be subjected to external forces or pressure (e.g., by being pressed or subjected to roll treatment). When carrying out such processing conditions, biomass or one or more anatomical parts can have a moisture content that approximates its natural moisture content (e.g., its moisture content immediately upon harvest), a moisture content achieved by adding moisture to the biomass or a moisture content that results from the drying of the biomass. For example, powdered, pulverized, ground or milled pieces of biomass or one or more anatomical parts can have moisture contents of less than about 25 weight percent, often less than about 20 weight percent, and frequently less than about 15 weight percent. Parts or pieces of biomass or one or more anatomical parts can be used as components of tobacco products without further processing, or alternatively the particulate biomass or anatomical part material can be processed further prior to incorporation into a tobacco product.

Harvested biomass or one or more anatomical parts, or components thereof, can be subjected to other types of processing conditions. For example, components of biomass or one or more anatomical parts can be separated from one another, or otherwise fractionated into chemical classes or mixtures of individual compounds. As used herein, an "isolated biomass component," "isolated component of one or more anatomical parts," "biomass isolate," or "isolate of one or more anatomical parts" is a compound or complex mixture of compounds separated from biomass or one or more anatomical parts of a plant of the *Nicotiana* species. The isolated biomass component or isolated component of one or more anatomical parts can be a single compound, a homologous mixture of similar compounds (e.g., isomers of a flavorful or aromatic compound), or a heterologous mixture of dissimilar compounds (e.g., a complex mixture of various compounds of different types, preferably having desirable sensory attributes).

Examples of the types of components that can be present in a biomass isolate or an isolate of one or more anatomical parts include various fatty acids and various triglycerides. Exemplary fatty acids include palmitic acid, linoleic acid, oleic acid, caprylic acid, myristic acid, pentadecanoic acid, palmetoleic acid, heptadecanoic acid, heptadecenoic acid, elaidic acid, gamma-lenolenic acid, arachidic acid, arachidonic acid, 11-eicosenoic acid, 8,11,14-eicosatrienoic acid, 11, 14,17-eicosatrienoic acid, 5,8,11,14,17-eicosopentanoic acid, heniecosenoic acid, lignoceric acid, 4,7,10,15,19-decosahexanoic acid, and stearic acid. Exemplary triglycerides include trilinolein, palmito-di-linolein, di-palmito-linolein, tripalmitin, tristearin, and triolein. Exemplary components of a biomass isolate or an isolate of one or more anatomical parts also include a variety of other compounds having flavor and aroma characteristics such as amino acids and various polyphenols.

Typical separation processes can include one or more process steps such as solvent extraction (e.g., using polar solvents, non-polar organic solvents, or supercritical fluids), chromatography, distillation, filtration, cold pressing or other pressure-based techniques, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated herein by reference. In addition, the biomass or components thereof can be subjected to the types of treatments set forth in Ishikawa et al., *Chem. Pharm. Bull.,* 50, 501-507 (2002); Tienpont et al., *Anal. Bioanal. Chem.,* 373, 46-55 (2002); Ochiai, *Gerstel Solutions Worldwide,* 6, 17-19 (2006); Coleman, III, et al., *J. Sci. Food and Agric.,* 84, 1223-1228 (2004); Coleman, III et al., *J. Sci. Food and Agric.,* 85, 2645-2654 (2005); Pawliszyn, ed., *Applications of Solid Phase Microextraction, RSC Chromatography Monographs,* (Royal Society of Chemistry, UK) (1999); Sahraoui et al., *J. Chrom.,* 1210, 229-233 (2008); and U.S. Pat. No. 5,301,694 to Raymond et al., which are incorporated herein by reference. See also, for example, the types of processing techniques set forth in Frega et al., *JAOCS,* 68, 29-33 (1991); Patel et al., *Tob. Res.,* 24, 44-49 (1998); Giannelos et al., *Ind. Crops Prod.,* 16, 1-9 (2002); Mukhtar et al., *Chinese J. Chem.,* 25, 705-708 (2007); Stanisavljevic et al., *Eur. J. Lipid Sci. Technol.,* 111, 513-518 (2009); which are incorporated herein by reference.

Other methods of forming a biomass isolate or an isolate of one or more anatomical parts from tobacco can be employed. For example, such a method can produce a lipid-containing isolate from a tobacco biomass or anatomical part source. Methods of extracting oil components from plant biomass or one or more anatomical parts are described, for example, in U.S. Pat. No. 4,008,210 to Steele et al.; U.S. Pat. No. 4,009,290 to Okumori et al.; U.S. Pat. No. 4,045,879 to Witte; U.S. Pat. No. 4,122,104 to Witte; U.S. Pat. No. 4,298,540 to Youn et al.; U.S. Pat. No. 4,359,417 to Karnofsky et al.; U.S. Pat. No. 4,456,556 to Grimsby; U.S. Pat. No. 4,456,557 to Grimsby; U.S. Pat. No. 4,466,923 to Friedrich; U.S. Pat. No. 4,515,726 to Sullivan; U.S. Pat. No. 4,847,106 to Pike et al.; U.S. Pat. No. 5,077,071 to Strop; U.S. Pat. No. 5,296,621 to Roos et al.; U.S. Pat. No. 5,397,571 to Roland et al.; U.S. Pat. No. 5,932,095 to Walters et al.; U.S. Pat. No. 6,083,729 to Martin et al.; U.S. Pat. No. 6,225,483 to Franke; U.S. Pat. No. 6,403,126 to Webster et al.; U.S. Pat. No. 6,414,172 to Garces et al.; U.S. Pat. No. 6,417,157 to Wadsworth et al.; U.S. Pat. No. 6,495,175 to Rao et al.; U.S. Pat. No. 6,504,085 to Howard; U.S. Pat. No. 6,860,998 to Wilde; U.S. Pat. No. 7,074,449 to Holley et al.; and U.S. Pat. No. 7,156,981 to Wilde et al.; and US Patent Appl. Pub. Nos. 2002/0121628 to Kapila et al.; 2004/0009242 to Krasutsky et al.; 2005/0042347 to Bathurst et al.; 2005/0147722 to Fan et al.; and 2006/0111578 to Arhancet et al., all of which are incorporated by reference herein.

Components of biomass or of one or more anatomical parts can be subjected to conditions so as to cause those components (whether as part of the biomass or of the one or more anatomical parts or in the form of an isolated component) to undergo chemical transformation. For example, a biomass isolate or an isolate of one or more anatomical parts that has been separated from the biomass or one or more anatomical parts can be treated to cause chemical transformation or can be admixed with other ingredients. Such chemical transformation or modification can result in changes of certain chemical and physical properties of such biomass isolate or isolate of one or more anatomical parts (e.g., sensory attributes of such an isolate). Exemplary chemical modification processes can be carried out by acid/base reaction, hydrolysis, heating (e.g., a thermal treatment where the isolate is subjected to an elevated temperature such as a temperature of at least about 50° C. or at least about 75° C. or at least about 90° C.), and enzymatic treatments (e.g., using hydrolyase, glycosidase, or glucocidase); and as such, components of the isolate can undergo esterification, transesterification, isomeric conversion, acetal formation, acetal decomposition, and the like. Additionally, various isolated lipid components of the biomass or one or more anatomical parts can be subjected to hydrogenation in order to alter the degree of saturation of those components, and hence alter the physical form or behavior of those components.

In one aspect, biomass or one or more anatomical parts can be cold pressed in order to squeeze lipids from the biomass or one or more anatomical parts, and those lipid components are collected and isolated; or alternatively the biomass or one or more anatomical parts can be subjected to solvent extraction using a solvent (e.g., a polar solvent or a non-polar organic solvent), and the resulting extract is collected and the extracted components are isolated. Then, any of the various biomass components or components of one or more anatomical parts may be subjected to enzymatic treatment to form an enzymatically-treated material. The enzymatically-treated material then is subjected to solvent extraction to form a biomass isolate or an isolate of one or more anatomical parts.

In one embodiment, the separating or isolating process comprises freezing harvested biomass or one or more anatomical parts or a portion thereof to form a frozen biomass or anatomical part material, processing the frozen biomass or anatomical part material into a particulate form, subjecting the particulate biomass or anatomical part material to an enzymatic treatment to chemically alter the particulate biomass or anatomical part material, and extracting the particulate biomass or anatomical part material with a solvent to produce a biomass isolate or an isolate of one or more anatomical parts. Exemplary enzymatic treatments include treatment with a glycosidase or a glucosidase.

The biomass or one or more anatomical parts and components or isolates thereof are useful as components for tobacco compositions, particularly tobacco compositions incorporated into smoking articles or smokeless tobacco products. Addition of such components according to the invention to a tobacco composition can enhance a tobacco composition in a variety of ways, depending on the nature of the biomass or seed isolate and the type of tobacco composition. Exemplary such components can serve to provide flavor and/or aroma to a tobacco product (e.g., composition that alters the sensory characteristics of tobacco compositions or smoke derived therefrom).

The form of biomass isolate or isolate of one or more anatomical parts can vary. Typically, such isolate is in a solid, liquid, or semi-solid or gel form. Biomass or seed isolate can be used in concrete, absolute, or neat form. Such isolate can have a dry particulate form, a waxy form, or a thick paste form. Liquid forms include isolates contained within aqueous or organic solvent carriers.

The biomass or one or more anatomical parts, processed biomass or one or more anatomical parts, and biomass isolates or isolates from one more anatomical parts can be employed in a variety of forms. Biomass or one or more anatomical parts, or an isolate of biomass or of one or more anatomical parts, can be employed as a component of processed tobaccos. In one regard, the biomass or one or more anatomical parts, or components thereof, can be employed within a top dressing formulation, or within a casing formulation for application to tobacco strip (e.g., using the types of manners and methods set forth in U.S. Pat. No. 4,819,668 to Shelar, which is incorporated herein by reference). Alternatively, the biomass or one or more anatomical parts, or components thereof, can be employed as an ingredient of a reconstituted tobacco material (e.g., using the types of tobacco reconstitution processes generally set forth in U.S. Pat. No. 5,143,097 to Sohn; U.S. Pat. No. 5,159,942 to Brinkley et al.; U.S. Pat. No. 5,598,868 to Jakob; U.S. Pat. No. 5,715,844 to Young; U.S. Pat. No. 5,724,998 to Gellatly; and U.S. Pat. No. 6,216,706 to Kumar, which are incorporated herein by reference). The biomass or one or more anatomical parts, or components thereof, also can be incorporated into a cigarette filter (e.g., in the filter plug, plug wrap, or tipping paper) or incorporated into cigarette wrapping paper, preferably on the inside surface, during the cigarette manufacturing process. An isolate from biomass or from one or more anatomical parts which isolate has a waxy or smooth texture can be used as a coating for the surface of a formed smokeless tobacco product. An isolate having sticky properties can be used as an adhesive (or component of an adhesive) or binding agent within tobacco products. An isolate having a oily or liquid character can be used as a solvent (e.g., to be used to replace, or act comparable to, a triglyceride type of solvent; or to replace a glycol type of solvent as a humectant or as a carrier for casing components).

The biomass or one or more anatomical parts, processed biomass or one or more anatomical parts, and biomass isolates or isolates from one more anatomical parts can be incorporated into smoking articles. The biomass or one or more anatomical parts, processed biomass or one or more anatomical parts, and biomass isolates or isolates from one more anatomical parts can be admixed with other components that are employed in the manufacture of tobacco products. Exemplary types of further ingredients that can be admixed with the biomass or anatomical part material include flavorants, fillers, binders, pH adjusters, buffering agents, colorants, disintegration aids, antioxidants, humectants and preservatives. Representative tobacco blends, non-tobacco components, and representative cigarettes manufactured therefrom, are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,220,930 to Gentry; and U.S. Pat. No. 5,360,023 to Blakley et al.; US Pat. Appl. Pub. No. 2002/0000235 to Shafer et al.; and PCT WO 02/37990. Those tobacco materials also can be employed for the manufacture of those types of cigarettes that are described in U.S. Pat. No. 4,793,365 to Sensabaugh; U.S. Pat. No. 4,917,128 to Clearman et al.; U.S. Pat. No. 4,947,974 to Brooks et al.; U.S. Pat. No. 4,961,438 to Korte; U.S. Pat. No. 4,920,990 to Lawrence et al.; U.S. Pat. No. 5,033,483 to Clearman et al.; U.S. Pat. No. 5,074,321 to Gentry et al.; U.S. Pat. No. 5,105,835 to Drewett et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,247,949 to Deevi et al.; U.S. Pat. No. 5,551,451 to Riggs et al.; U.S. Pat. No. 5,285,798 to Banerjee et al.; U.S. Pat. No. 5,593,792 to Farrier et al.; U.S. Pat. No. 5,595,577 to Bensalem et al.; U.S. Pat. No. 5,816,263 to Counts et al.; U.S. Pat. No. 5,819,751 to Barnes et al.; U.S. Pat. No. 6,095,153 to Beven et al.; U.S. Pat. No. 6,311,694 to Nichols et al.; and U.S. Pat. No. 6,367,481 to Nichols et al.; US Pat. Appl. Pub. No. 2008/0092912 to Robinson et al.; and PCT WO 97/48294 and PCT WO 98/16125. See, also, those types of commercially marketed cigarettes described *Chemical and Biological Studies on New Cigarette Prototypes that Heat Instead of Burn Tobacco*, R. J. Reynolds Tobacco Company Monograph (1988) and *Inhalation Toxicology*, 12:5, p. 1-58 (2000).

The *Nicotiana* biomass or one or more anatomical parts, processed biomass or one or more anatomical parts, and biomass isolates or isolates from one more anatomical parts can be incorporated into smokeless tobacco products, such as loose moist snuff, loose dry snuff, chewing tobacco, pelletized tobacco pieces (e.g., having the shapes of pills, tablets, spheres, coins, beads, obloids or beans), extruded or formed tobacco strips, pieces, rods, cylinders or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips (e.g., US Pat. App. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtoniam fluid or a thixotropic fluid incorporating tobacco of some form). Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. App. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See also, the types of smokeless tobacco formulations, ingredients, and processing methodologies set forth in U.S. Pat. No. 6,953,040 to Atchley et al. and U.S. Pat. No. 7,032,601 to Atchley et al.; US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

The residue of biomass or anatomical part material remaining after subjecting biomass or anatomical part material to a separation process (e.g., cold pressing or solvent extraction) and removing some portion of the biomass or one or more anatomical parts can also be incorporated into a tobacco product, including any of the tobacco products mentioned herein with regard to biomass or one or more anatomical parts, or isolates therefrom. For example, a residue remaining after cold pressing biomass or one or more anatomical parts and removing lipid components can be used as a tobacco composition component (e.g., as part of a reconstituted tobacco material), and incorporated into a smoking article or a smokeless tobacco composition. The insoluble pulp residue remaining after solvent extraction of a solvent-soluble portion of a biomass or anatomical part material can likewise be used as a component of a tobacco composition.

Certain isolates, such as triglyceride-containing isolates of biomass or of one or more anatomical parts, can be used as components of capsules used in smoking articles or smokeless tobacco compositions. In particular, triglyceride-containing isolates can be combined with a flavorant and used as a diluting agent or carrier within the internal payload of certain breakable capsules. Typically, such a capsule according to the invention has an outer wall and an internal liquid, solid, or gel payload. The payload is released upon rupture of the capsule wall. Exemplary capsule-containing tobacco products that could incorporate such isolates are set forth in US Pat. Appl. Pub. Nos. 2004/0261807 to Dube et al.; 2005/0066982 to Clark et al.; 2007/0186941 to Holton et al.; 2008/0302373 to Stokes et al.; and 2009/0050163 to Hartmann et al., each of which is incorporated herein by reference.

Aspects of the present invention are more fully illustrated by the following example, set forth to illustrate certain aspects of the present invention and not to be construed as limiting thereof.

In connection with the invention it is found that glycerin is readily derived through hydrolytic treatment of chemically or physically untransformed or transformed biomass or seed from the *Nicotiana* species. Acid-catalyzed hydrolysis or base-catalyzed hydrolysis ("saponification") is suitable for such production of glycerin. Additionally, enzymatic treatment with a lipase or other suitable enzyme is useful for such production.

In an embodiment, seed is collected from mature *Nicotiana* plants. The seed is ground into a powder, and the powder is extracted with hexane. Solvent is then evaporated from the hexane fraction, whether with heat, or at ambient temperature, or through the use of an azeotrope, leaving an oleaginous mass. The oleaginous mass is dissolved in a suitable amphipathic solvent to form an intermediate mixture. A volume of either an alkali metal hydroxide or a mineral acid is then added to the intermediate mixture, and reaction is allowed to proceed, in which glycerol and fatty acids are formed. Excess solvent is then evaporated, leaving a product mixture. The product mixture is extracted with a nonpolar solvent, in which case the bulk of glycerol product remains in the residue, or with a polar solvent, in which case the bulk of glycerol product is extracted.

In an embodiment, the invention provides a method for producing glycerin from tobacco, the method comprising contacting an acylglycerol-containing starting material derived from a tobacco plant with a composition comprising an alkali metal hydroxide or a mineral acid for a period of time sufficient for at least some of the acylglycerol contained in the starting material to be hydrolyzed, thereby producing fatty acids and glycerin.

In an embodiment, the invention provides an article of manufacture comprising glycerin derived from plants or portions of plants from the *Nicotiana* species by hydrolytic treatment of the plants or portions of plants.

According to the invention, a mineral acid for use in hydrolytic treatment of plants or portions of plants from the *Nicotiana* species may comprise an industrially acceptable mineral acid and may particularly comprise a mineral acid selected from sulfuric acid and hydrochloric acid.

According to the invention, an alkali metal hydroxide for use in hydrolytic treatment of plants or portions of plants from the *Nicotiana* species may comprise an industrially acceptable alkali metal hydroxide and may particularly comprise sodium hydroxide or potassium hydroxide.

According to the invention, conditions for contacting at least a portion of one or more plants from the *Nicotiana* species with a mineral acid or an alkali metal hydroxide may be chosen according to the discretion of one skilled in the art, such so-called reaction conditions including such variables as time of reaction, temperature pressure, pH, ionic strength, rate of mixing, agitation, sparging, aeration and so forth.

According to the invention, conditions for isolating acetate from at least a portion of one or more plants from the *Nicotiana* species may be chosen according to the discretion of one skilled in the art, including conditions for distillation, filtration or other separation, and so forth.

According to the invention, conditions for reacting acetic acid isolated from at least a portion of one or more plants from the *Nicotiana* species with glycerol isolated from at least a portion of one or more plants from the *Nicotiana* species may be chosen according to the discretion of one skilled in the art, such so-called reaction conditions including such variables as time of reaction, temperature pressure, pH, ionic strength, rate of mixing, agitation, sparging, aeration and so forth.

According to the invention, any industrially acceptable treatment, or no treatment, of at least a portion of one or more plants from the *Nicotiana* species may be suitable for use of at least a portion of one or more plants from the *Nicotiana* species in making a composition according to the invention, in a method according to the invention, or making an article of manufacture according to the invention.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method for producing triacetin from one or more plants of genus *Nicotiana*, the method comprising: (a) contacting an acylglycerol-containing first starting material derived from one or more plants of genus *Nicotiana* with a composition comprising an alkali metal hydroxide, an alkaline earth oxide or hydroxide, a mineral acid, or an esterase for a period of time sufficient for at least some of the acylglycerol contained in the starting material to be hydrolyzed, thereby producing an intermediate comprising glycerin; (b) isolating glycerin from the intermediate comprising glycerin to form an isolated glycerin reactant; (c) subjecting an acetate-containing second starting material derived from one or more plants of genus *Nicotiana* to destructive distillation, thereby producing an intermediate comprising acetic acid; (d) isolating acetic acid from the intermediate comprising acetic acid to form an isolated acetic acid reactant; (e) contacting a quantity of the isolated glycerin reactant with a quantity of the isolated acetic acid reactant under conditions favoring esterification, thereby producing triacetin.

2. The method of claim 1, wherein the acetate-containing second starting material starting material is derived from tobacco.

3. The method of claim 2, wherein the acetate-containing second starting material is derived from tobacco biomass.

4. The method of claim 1, wherein the conditions favoring esterification comprise contacting each reactant with a transition metal oxide.

5. The method of claim 4, wherein the transition metal oxide is selected from the group consisting of: $ZrO_2$, $WO_3$, $TiO_2$, $MoO_3$.

6. The method of claim 1, wherein the conditions favoring esterification are acidic conditions.

7. The method of claim 6, wherein the acidic conditions comprise contacting each reactant with concentrated sulfuric acid.

8. The method of claim 5, wherein the transition metal oxide is $ZrO_2$.

9. The method of claim 5, wherein the transition metal oxide is $WO_3$.

10. The method of claim 5, wherein the transition metal oxide is $TiO_2$.

11. The method of claim 5, wherein the transition metal oxide is $MoO_3$.

12. A method for producing triacetin from one or more plants of genus *Nicotiana*, the method comprising: (a) contacting an acylglycerol-containing first starting material derived from one or more plants of genus *Nicotiana* with a composition comprising an alkali metal hydroxide, an alkaline earth oxide or hydroxide, a mineral acid, or an esterase for a period of time sufficient for at least some of the acylglycerol contained in the starting material to be hydrolyzed, thereby producing an intermediate comprising glycerin; (b) isolating glycerin from the intermediate comprising glycerin to form an isolated glycerin reactant; (c) subjecting an acetate-containing second starting material derived from one or more plants of genus *Nicotiana* to destructive distillation, thereby producing an intermediate comprising acetic acid; (d) isolating acetic acid from the intermediate comprising acetic acid to form an isolated acetic acid reactant; (e) contacting a quantity of the isolated glycerin reactant with a quantity of the isolated acetic acid reactant under conditions favoring esterification, wherein the conditions favoring esterification comprise contacting each reactant with a transition metal oxide, thereby producing triacetin.

13. The method of claim 12, wherein the transition metal oxide is $ZrO_2$.

14. The method of claim 12, wherein the transition metal oxide is $WO_3$.

15. The method of claim 12, wherein the transition metal oxide is $TiO_2$.

16. The method of claim 12, wherein the transition metal oxide is $MoO_3$.

17. A method for producing triacetin from tobacco biomass, the method comprising: (a) contacting an acylglycerol-containing first starting material derived from tobacco biomass with a composition comprising an alkali metal hydroxide, an alkaline earth oxide or hydroxide, a mineral acid, or an esterase for a period of time sufficient for at least some of the acylglycerol contained in the starting material to be hydrolyzed, thereby producing an intermediate comprising glycerin; (b) isolating glycerin from the intermediate comprising glycerin to form an isolated glycerin reactant; (c) subjecting an acetate-containing second starting material derived from tobacco biomass to destructive distillation, thereby producing an intermediate comprising acetic acid; (d) isolating acetic acid from the intermediate comprising acetic acid to form an isolated acetic acid reactant; (e) contacting a quantity of the isolated glycerin reactant with a quantity of the isolated acetic acid reactant under conditions favoring esterification, wherein the conditions favoring esterification comprise contacting each reactant with a transition metal oxide, thereby producing triacetin.

18. The method of claim 17, wherein the composition comprises an alkali metal hydroxide.

19. The method of claim 17, wherein the composition comprises an alkaline earth oxide or hydroxide.

20. The method of claim 17, wherein the composition comprises a mineral acid or an esterase.

\* \* \* \* \*